(12) United States Patent
Götze et al.

(10) Patent No.: US 7,624,695 B2
(45) Date of Patent: Dec. 1, 2009

(54) TESTING DEVICE FOR HULL SHELLS

(75) Inventors: Matthias Götze, Dresden (DE); Mirko Sachse, Dresden (DE); Roald Best, Dresden (DE); Udo Berthold, Dresden (DE); Georg Grötzschel, Dresden (DE)

(73) Assignee: IMA Materialforschung und Anwendungstechnik GmbH, Dresden (DE)

( * ) Notice: Subject to any disclaimer, the term of this patent is extended or adjusted under 35 U.S.C. 154(b) by 18 days.

(21) Appl. No.: 11/693,044

(22) Filed: Mar. 29, 2007

(65) Prior Publication Data

US 2007/0227434 A1  Oct. 4, 2007

(30) Foreign Application Priority Data

Mar. 29, 2006 (DE) .................. 10 2006 015 642

(51) Int. Cl.
*B63B 3/00* (2006.01)
(52) U.S. Cl. .................. 114/355; 73/851; 73/852
(58) Field of Classification Search ........... 114/219, 114/355, 356, 357; 73/825, 849, 850, 851, 73/852, 853, 854, 730, 731
See application file for complete search history.

(56) References Cited

U.S. PATENT DOCUMENTS

| | | | |
|---|---|---|---|
| 2,383,491 A * | 8/1945 | Kemmer et al. ............. 73/798 |
| 2,775,116 A | 12/1956 | Bonell | |
| 4,759,812 A | 7/1988 | Miller | |
| 4,976,136 A | 12/1990 | Willan | |
| 5,431,061 A * | 7/1995 | Bertelsen et al. .............. 73/852 |
| 5,528,155 A | 6/1996 | King | |
| 6,158,666 A | 12/2000 | Banks | |
| 6,691,580 B1 * | 2/2004 | Bertelsen .................. 73/730 |

(Continued)

FOREIGN PATENT DOCUMENTS

DE  197 27 754 A1  1/1999

(Continued)

OTHER PUBLICATIONS

Ambur et al., Design and Evaluation of Composite Fuselage Panels Subjected to Combined Loading Conditions, Journal of Aircraft, Bd. 42, Nr. 4, 2005, XP008082679, pp. 1037-1045.

(Continued)

*Primary Examiner*—Lars A Olson
(74) *Attorney, Agent, or Firm*—Antonelli, Terry, Stout & Kraus, LLP.

(57) ABSTRACT

The invention relates to a testing device for hull shells, wherein the test specimen is joined to a complementary structure with legs, having a U-shape in cross section, and at the ends of the legs there are provided lengthwise flanges in the lengthwise direction of the complementary structure with means of attaching the hull shell to the complementary structure and of applying and absorbing corrective forces, while at the borders of the complementary structure in the lengthwise direction there are provided transverse flanges for applying and absorbing of test forces in six degrees of freedom. The complementary structure (1) is formed as a soft box of composite materials and the U-shaped cross section of the complementary structure (1) consists of a horizontal straight segment (11) and two ellipsoidal segments (12) adjoining each side, forming the legs (3) of the U-shaped complementary structure (1).

19 Claims, 7 Drawing Sheets

U.S. PATENT DOCUMENTS

| | | |
|---|---|---|
| 2001/0054228 A1 | 12/2001 | Lehmker |
| 2003/0146346 A1 | 8/2003 | Chapman |
| 2006/0101921 A1 | 5/2006 | Ostgaard |

FOREIGN PATENT DOCUMENTS

| | | |
|---|---|---|
| EP | 1 524 513 A | 4/2005 |
| EP | A-1683721 | 7/2006 |
| FR | 2 788 743 A | 7/2000 |
| RU | 1 798 654 A1 | 2/1993 |
| WO | WO 2007/053156 A | 5/2007 |

OTHER PUBLICATIONS

International Preliminary Report dated Nov. 27, 2008.
EP Search Report No. 08104311.9 dated Oct. 7, 2008.

* cited by examiner

Figure 6:
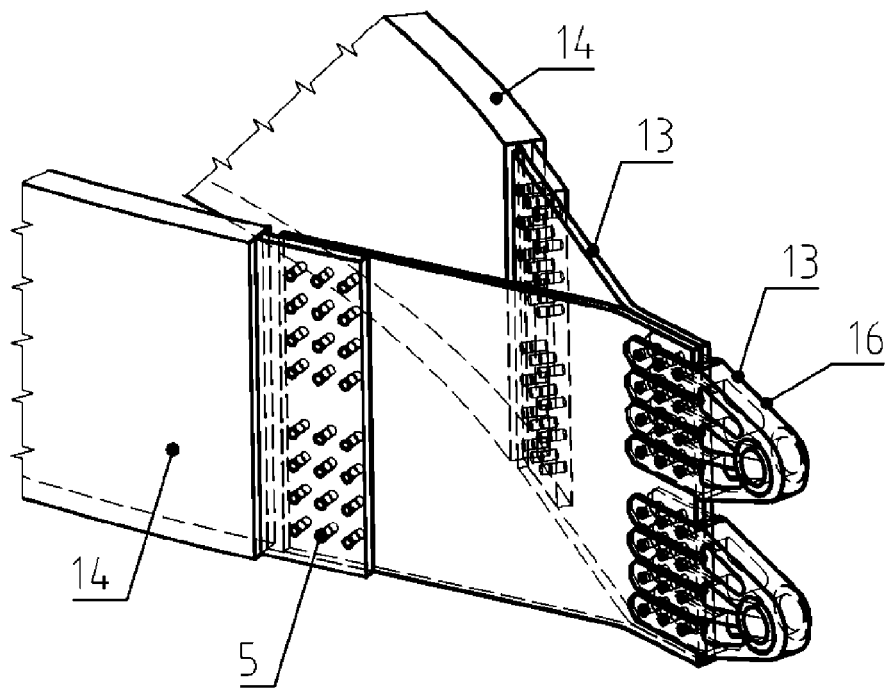
Figure 6:
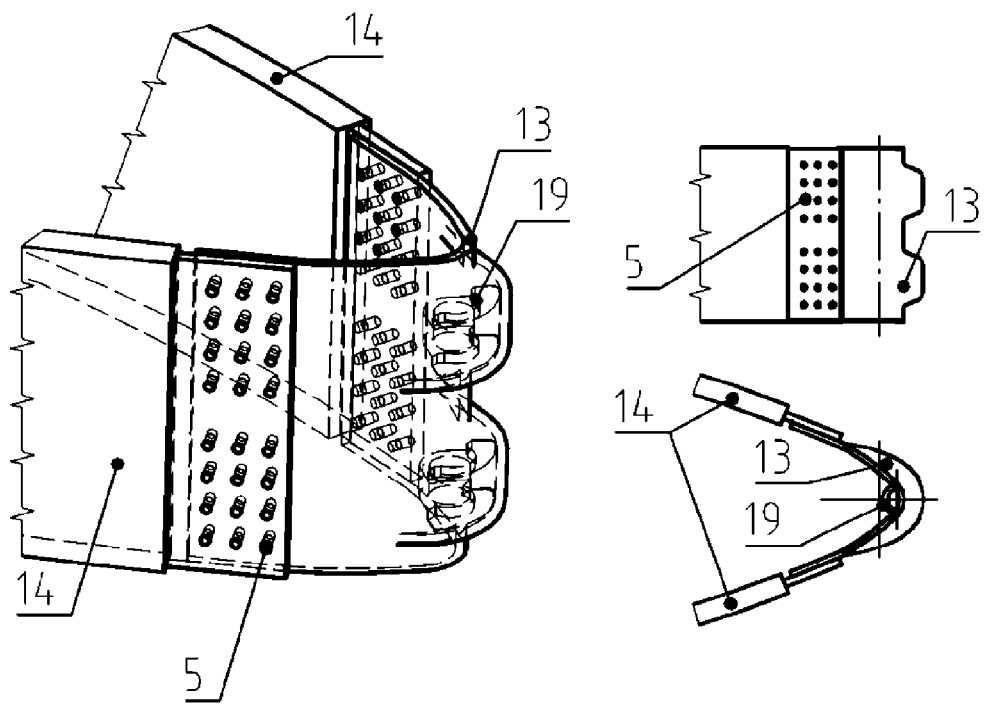

Figure 6 c) top
d) bottom

TESTING DEVICE FOR HULL SHELLS

The invention relates to a testing device for hull shells and is especially suitable for dynamic testing of hull shells.

By a hull shell is meant, quite generally, a two-dimensional object, which is exposed by means of the testing device to various loads and superimposed combinations of loads for the purpose of testing the properties of the structural parts. The hull shell, as a test specimen, is usually part of a complex support system which, because of its size, as in the case of aircraft hulls, cannot entirely be subjected to efficient testing of the properties of its structural parts.

Such testing devices are thus used to investigate individual parts that need to be subjected to realistic strains in order to successfully demonstrate the structural properties required for permits or the like. Furthermore, the testing devices are used for static and dynamic studies on aircraft hulls, for example, during the development process.

The hull shells are made, for example, from composite materials, especially fiber composite structures. By composite materials and especially fiber composite materials is meant, for example, carbon fiber reinforced plastic (CFP) or fiberglass-reinforced plastic (FGP), or also FGP/aluminum composites.

The test specimens are usually plane load-bearing structures which are geometrically, i.e., structurally anisotropic, and also in terms of material. They are characterized by multiaxial, line-type cutting load curves and resulting multi-axial strain states. In order to expose the specimens to realistic tests, one must investigate at least three load axes. This involves the longitudinal expansion, the circumferential expansion, and the shearing yield. Furthermore, local influences are simulated from excess internal pressure in airplanes, reflecting the action of the stiffness distribution of the hull structure when flying at high altitudes.

In the field of structural parts testing devices for fuselage shells, hereinafter termed hull shells, various concepts are familiar.

According to DE 103 44 855 B4, for example, a pressure-shear layout is known for applying high shear loads, whereby the pressure and shear loads act in the same direction and can be applied by separate adjustable elements. The drawback to this device is that a two-dimensional air pressure loading or the alternative tensile force superpositioning cannot be implemented with this device.

The prior art includes test devices for hull shells which enable air pressure loading of the hull shells. Thus, in DE 197 027 754 A1, a device is known for restraining and testing of objects, especially parts of fuselage shells. The hull shells are exposed here to various dynamic loadings at the same time. In particular, there is a tensile loading in the lengthwise direction of the hull shell and a two-dimensional air pressure loading, produced by a pressure difference between the interior of the airplane and the outer surroundings.

The drawback with these testing devices is that they each in themselves make possible load combinations which could only cover the separate testing of all cylindrical regions of the hull in full extent, i.e., close to the operational loads, if applied jointly. But the proposed methods for this, even with modifications, are much too physically restricted.

Secondly, it should be noted that the devices according to DE 197 027 754 A1 in the case of excess pressure load, due to their underlying principle, can only imperfectly model the sector symmetry. That is, a distribution of bending moments is created that is acceptable for thin fuselage skin.

Traditionally, thus, one uses devices in which the hull shells are mounted in a floating manner, in which a frequent drawback is the strongly fluctuating stress distribution. What is more, separate application of circumferential and shear loads results in a testing of poorer quality.

Thus, on the whole, shear yield tests are impossible, or deficient, with traditional multiaxial testing devices using floating mounted shells, and, furthermore, the superpositioning of stresses also cannot be simulated to a sufficient degree.

Based on this prior art, testing devices are also known to overcome the mentioned drawbacks, being known in technical circles as D-boxes. In Ambur, D., Rouse, M.: Design and Evaluation of Composite Fuselage Panels Subjected to Combined Loading Conditions. In: Journal of Aircraft, Vol. 42, No. 4, July-August 2005, a D-box is disclosed, showing a cross section for the complementary structure in the shape of a circular arc segment.

Configuring the D-box with a cross section in the shape of a circular arc segment involves various drawbacks. In particular, one should mention that a preferably rigid coupling between the shell and the complementary structure is not possible without high stress perturbations, due to the stiffness conditions. The result is a jointed design of the edges at the longitudinal margin. This is implemented by means of discrete hinges between the individual beams. The consequence is a substantial limitation of the possible test missions, particularly high shear stress and residual strength studies in general. The limitation comes from the structurally dictated stress concentrations of the discrete design.

The corrective measures in the secant direction of the equivalent cross section can only be set at one working point of the load cycles—passive braces.

A further drawback is that the circular arc segment shape of the cross section of the D-box in the prior art leads to an increased space requirement.

Generally speaking, the D-box is a structure shaped like a D in cross section, in which the so-called "soft box" forms the complementary structure to the hull shell. For the testing, the hull shell is connected mechanically discretely and jointed to the "soft box".

However, another drawback is that composite materials cannot be studied with adequate safety and reliability in test devices with a "soft box" made of metal, since the metal has a yield limit, which is not typical of composite materials, and thus the desired test region cannot be achieved. A further drawback of the known test devices is that frame forces cannot be applied.

The goal of the present invention is to provide a device for efficient testing of shell elements that implements a realistic measurement of shear yield stresses, as well as superpositioning of several kinds of stress, and the test device should also be cost-efficient in use.

The goal is achieved by a test device for hull shells in which the testing involves a complementary structure.

In a first embodiment of the invention, which is known as a soft box inside the D-box, the complementary structure is U-shaped in cross section and has supports—lengthwise flanges—at the ends of the legs in the lengthwise direction of the complementary structure, with means for attachment of the hull shell to the complementary structure, and also for applying of corrective forces and transmitting of test forces. The means for attachment of the hull shell are characterized by a special combination of positive connection and frictional connection, for purposes of interchangeable structure/changing of test specimens. The means for attaching the hull shell to the complementary structure are designed to apply and absorb test cutting forces in the transverse and lengthwise direction.

Arranged at the boundaries of the complementary structure in the lengthwise direction are transverse flanges, which serve to apply and absorb test forces in the circumferential direction, as well as auxiliary forces in the lengthwise direction. They make it possible to load the equivalent cross section—pressure pipes—in six degrees of freedom. The complementary structure is fashioned as a soft box of composite materials, in other words it is anisotropic in geometry and also in material, which furthermore eliminates the undesirable yield limits such as occur in test devices with complementary structures made of metal. The stress limits, especially the breaking elongations, are adjusted specifically in terms of those of the CFP test specimens.

According to one preferred embodiment of the invention, the complementary structure is made of fiberglass-reinforced epoxy resin. The lengthwise flanges at the ends of the legs in the sample embodiment are designed with an angle $\alpha_{SW}=22°$ to the connection line between the legs.

The general relation holds: $\alpha_{SW}=\alpha_{p\ddot{u}}-0.5°$, the index "SW" standing for sandwich and "pü" for the circular segment exposed to excess pressure.

The complementary structure is preferably formed on alternatingly lined up U-profiles in the lengthwise direction, so that a corrugated longitudinal cross section is produced. The material thickness of the complementary structure made from composites is preferably 13.6 mm for the first type of test shell—CFP sandwich shells—and the composite material of the complementary structure is constructed from up to 23 individual layers.

The invention is furthermore solved, alternatively, in that the test device for hull shells with a complementary structure is configured such that the equivalent cross section is defined from N-hull shells with N-shell couplers, where N is a whole number—di-, tri-, tetra-box.

The notion of the invention is based on the forming of an equivalent cross section that consists of one or more hull shells and a complementary structure, the complementary structure being formed by all elements of the equivalent cross section that are not hull shells. The equivalent cross section itself is enclosed, in order to form a pressurized container.

One merit of the notion of the invention is that one uses a complementary structure characterized by mechanical properties which are extremely direction-dependent. This aids in mastery of the dimensions and, thus, the attainable experimental quality of the surrounding test stand layout. At the same time, a very high resistance to local and global elongations is demanded of it. The transmitting or applying of circumferential breaking loads or shear breaking loads, as well as highly superimposed fractions of both components with superpositioning of around 75%, is made possible by the device according to the invention. At the same time, a detachable connection is provided between the hull shells and the complementary structure, which leads beneficially to a possible recycling of the complementary structures. According to the alternative embodiment of the invention, the complementary structure is formed proportionally by neighboring test specimens for a test specimen, which leads to an enormous time and cost efficiency for the test procedure, since one can test several specimens at the same time in a single test run. The device according to the invention is generally suited for the testing of fiber reinforced plastics (FRP), such as FGP or CFP.

By creating an equivalent cross section to reduce the required load applications—as compared to floating mounted test shells—many benefits are achieved. For example, the cross section is greatly reduced as compared to a barrel fuselage. Thus, with the devices of the invention one can perform testing which otherwise would require extremely large outlays for the test stand, due to the dimensions and orders of magnitude of the elements being tested.

In one preferred embodiment of the invention, the complementary structure shell coupler has a V-shaped cross section, consisting of two straight legs, which are joined together by a rounding. The rounding contains contact surfaces for application of correction forces by means of thrust-transmitting pieces.

In one alternative preferred embodiment of the invention, the complementary structure shell coupler has a Y-shaped cross section, consisting of two straight legs, joined together by a common straight extension. The extension contains means for applying discrete correcting forces by means of tension brackets or tension rods.

According to the invention, the equivalent cross section is defined in theory by one, two, three or four hull shells and soft pressure boxes, or the corresponding number of shell couplers, respectively.

The means of attaching the hull shell to the complementary structure are preferably formed by a funnel-like depression and a correspondingly shaped clamping disk, as well as screws and nuts, there being provided a ribbing of truncated pyramids on the top side of the clamping disk facing the hull shell.

The soft pressure box or the shell coupler are preferably made from fiberglass-reinforced epoxy resin and can be used for fracture experiments on carbon fiber reinforced plastics.

In one advantageous embodiment of the invention, one can test frame-reinforced hull shells with improved accuracy by providing a passive or active frame brace. The frame brace has an inner and outer leg—connected to a length adjustment, while the passive frame brace is fashioned so as to balance out the locally eccentric application of tangential forces. One should stress the merit that the relative angle between the frame heads remains approximately constant when the hull shell is placed under load.

An active frame brace likewise has an inner and outer leg—connected to a length adjustment—but contrary to the passive frame brace the inner leg is connected by a joint to the frame head and, furthermore, a correction actuator is arranged on the inner leg in parallel and connected to the piston rod via a second joint with the frame head so that the locally eccentric application of tangential forces is balanced out by the active frame brace. The relative angle between the frame heads remains constant or is hypercorrected under loading of the hull shell. Either the angle or the bending moment are used as the controlled variable and the dependent components are adjusted each time.

The merits of the device according to the invention can be summarized as follows:
reduction in active load application,
continuous edge tie-in→best possible force flow,
interchangeable design, despite rigid binding of test specimens,
use of variable sandwich thicknesses of test specimens,
higher frequency of experiments,
optimized sector symmetry under excess pressure load,
better quality of stress distribution,
passive load application for the frames, i.e., less control error,
all cylindrical hull segments are captured in the experimental simulation,
less energy required than for barrel experiment,
fewer number of samples for the same gain in knowledge, involving less waste, faster gain in knowledge, meaning less fuel consumption due to more optimized hull shells, shorter overall development process, leading to an improved competitive position.

It should be stressed in particular that the device according to the invention can also make use of distributed loads in the test in a reproducible manner, whereas with the D-box of the prior art one can only assign uniform circumferential loads. Furthermore, static destructive residual strength tests for all load components have been included in the performance range.

Figure 1:
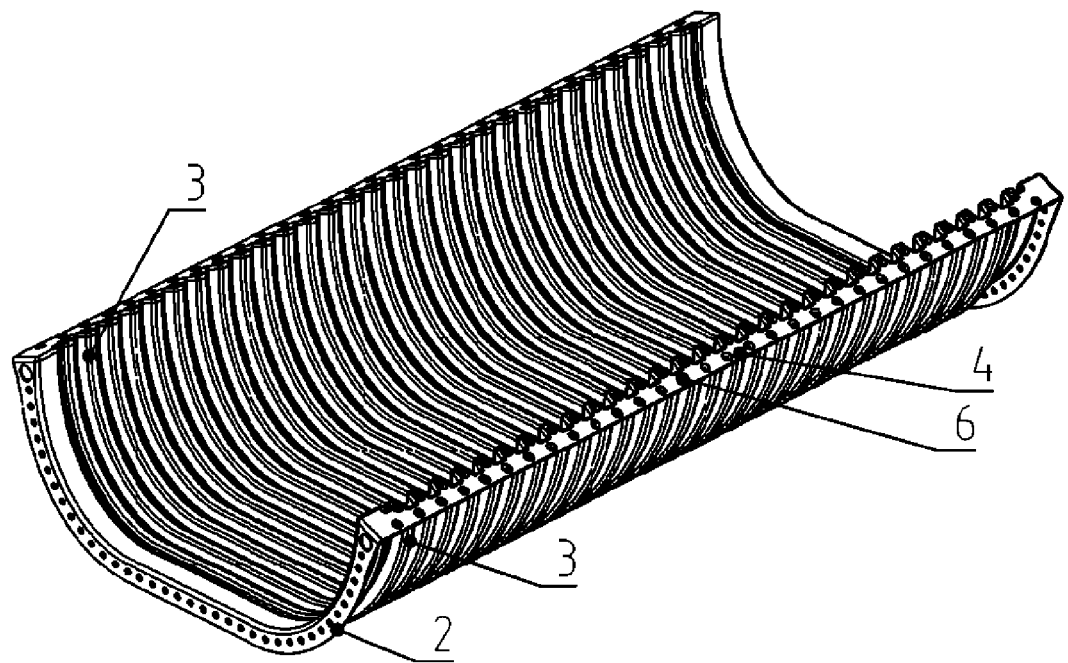
Figure 2:
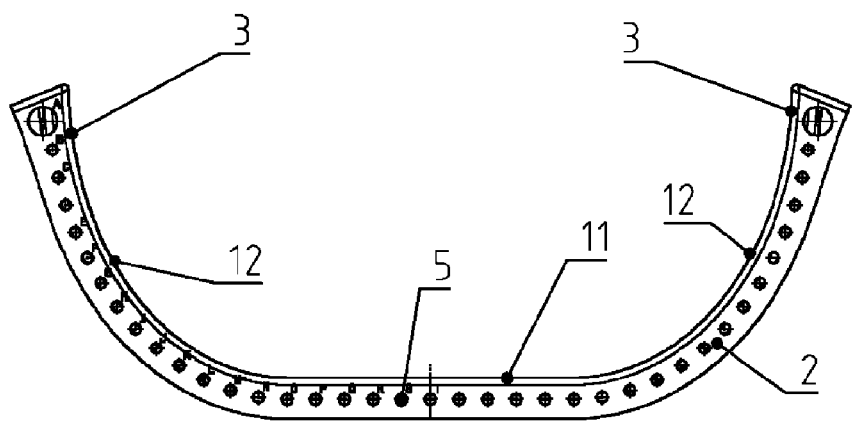
Figure 3:
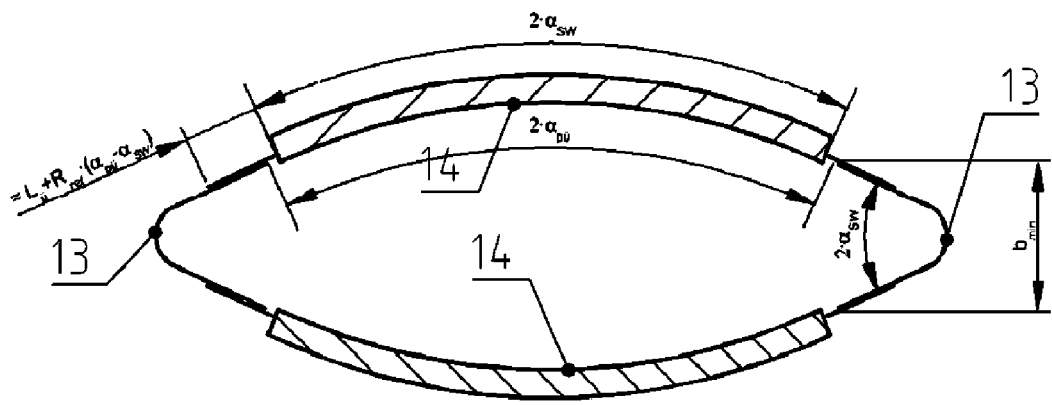
Figure 4:
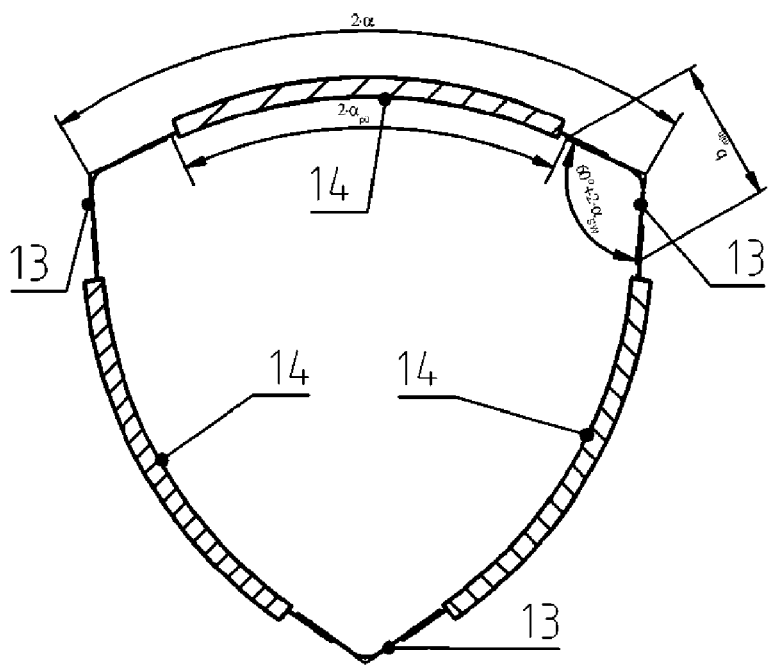
Figure 5:
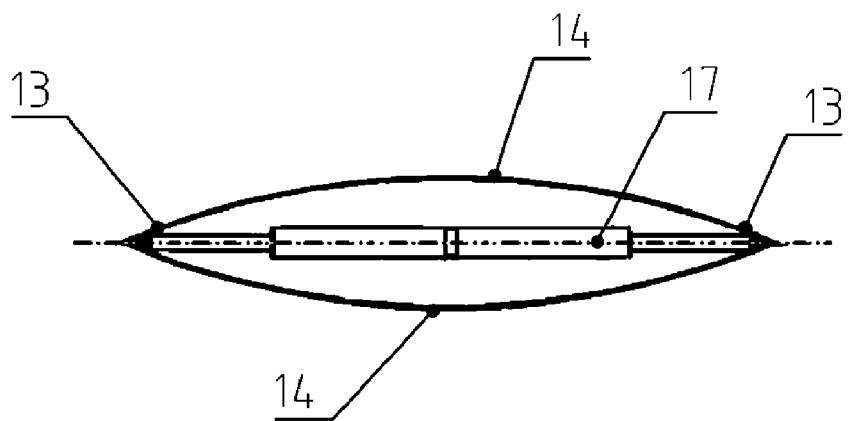
Figure 5:
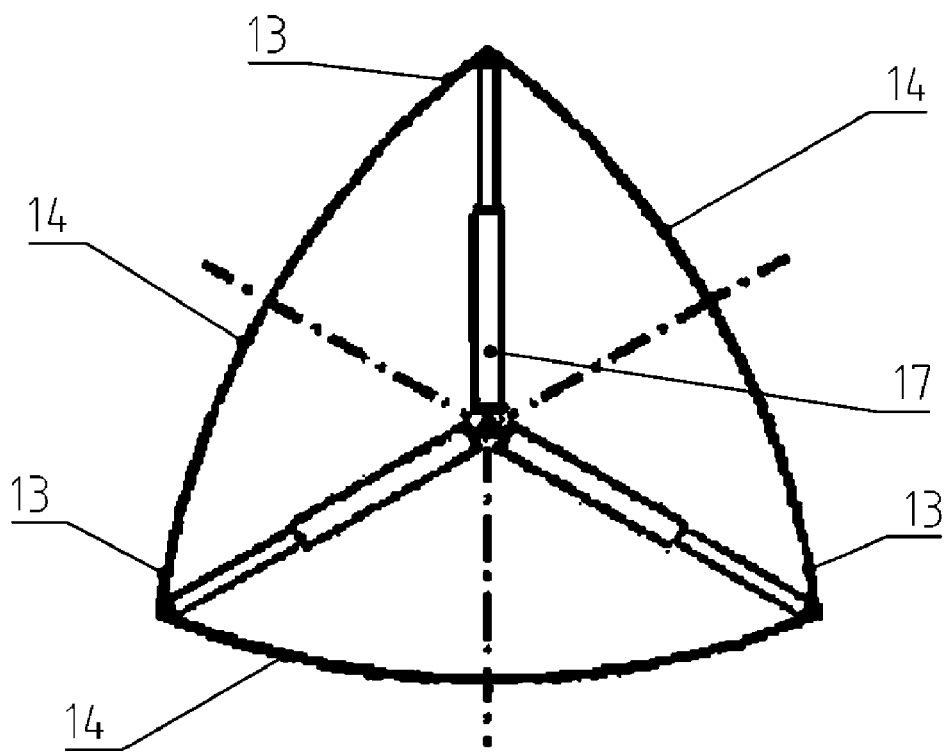
Figure 5:
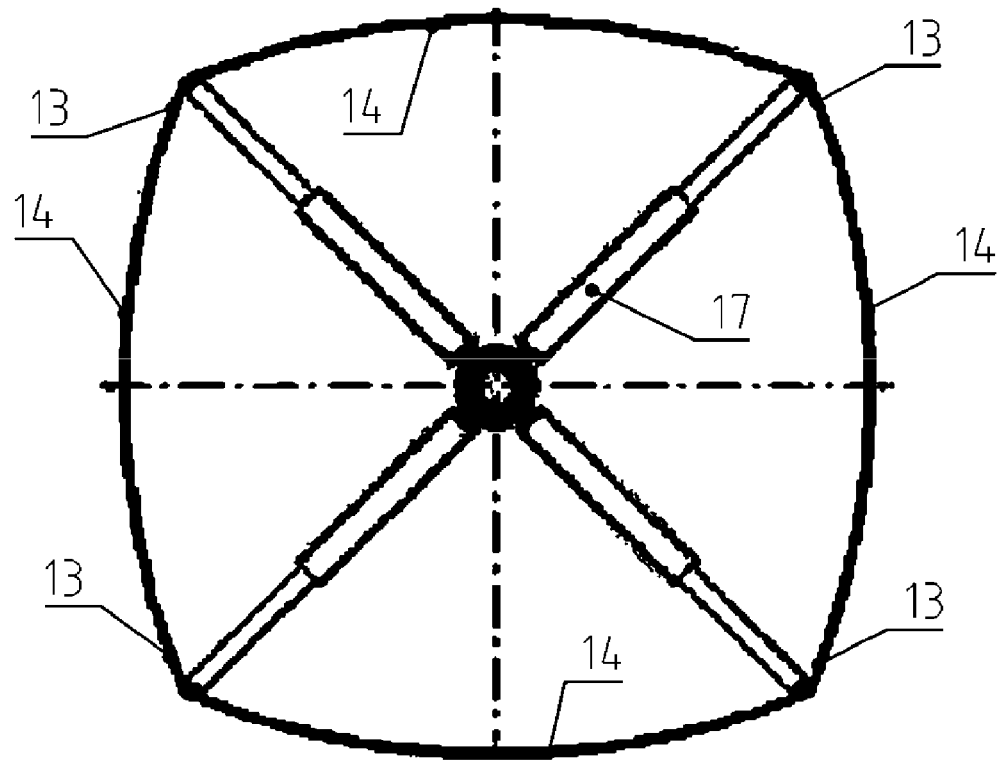
Figure 7:
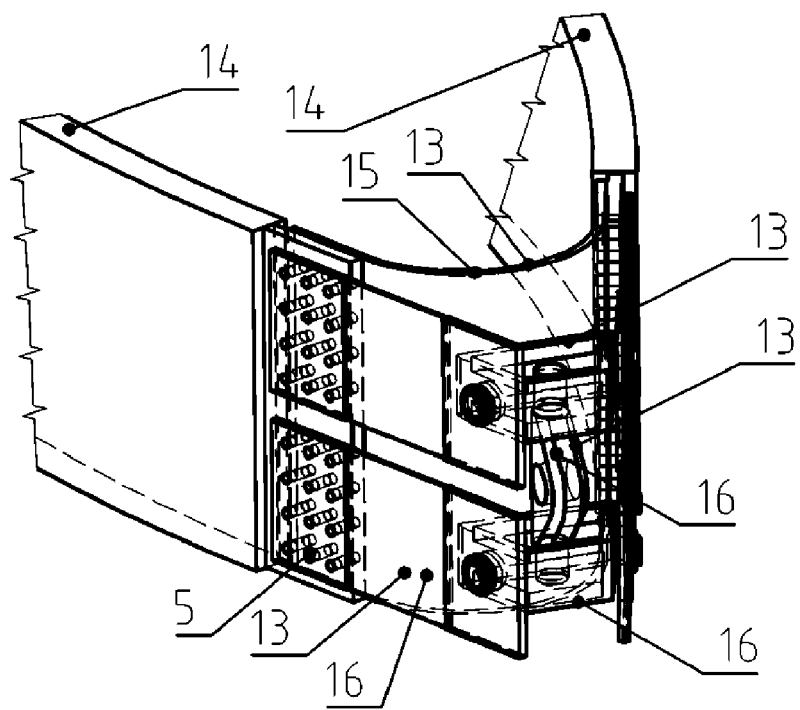
Figure 8:
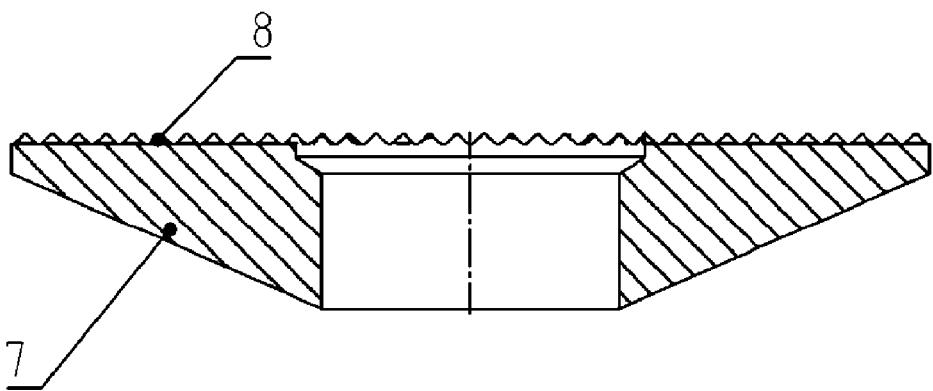
Figure 8:
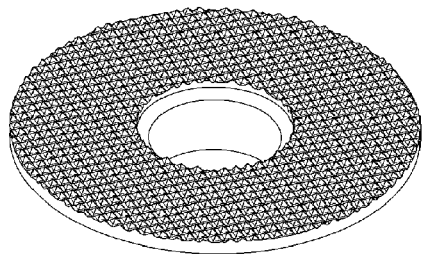
Figure 8:
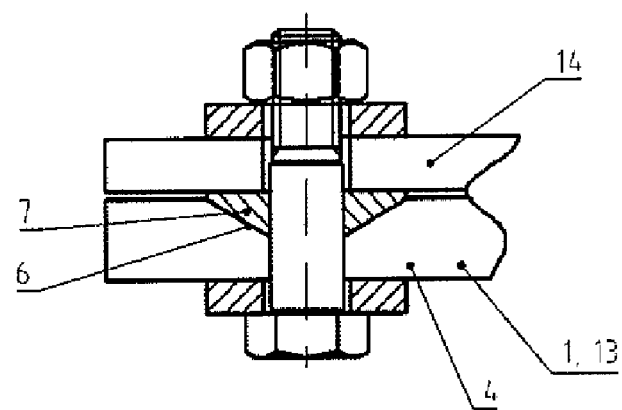
Figure 9:
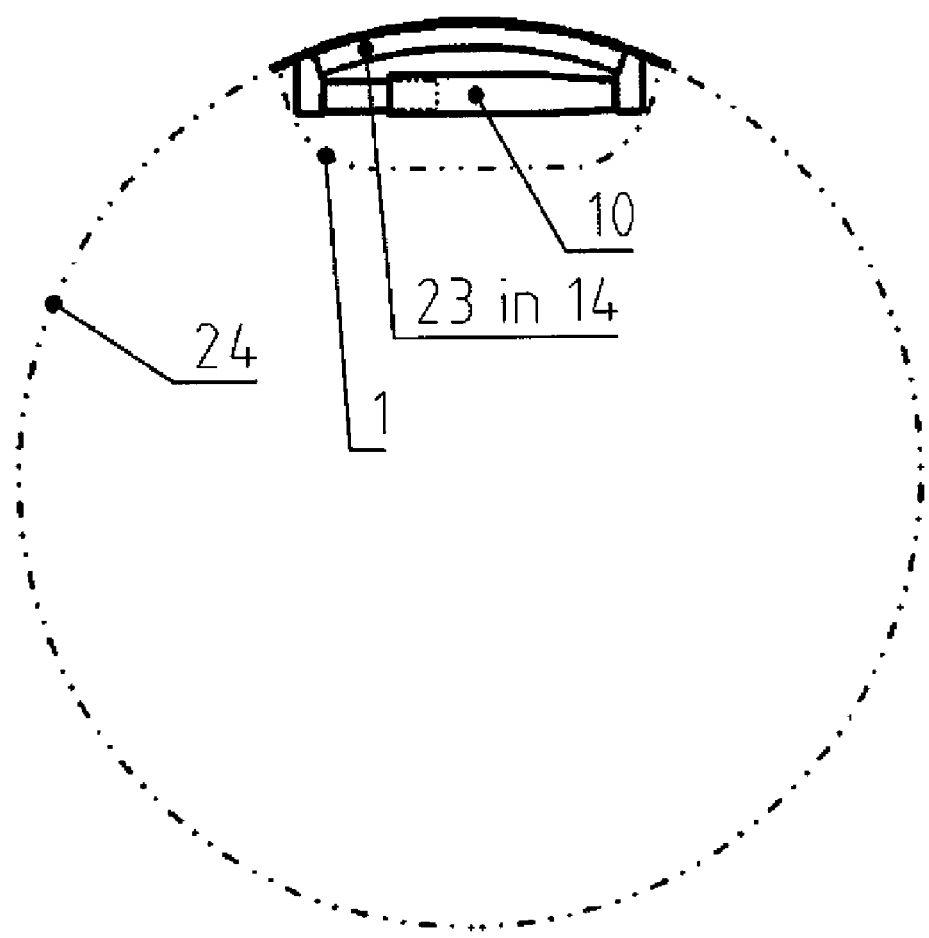
Figure 10:
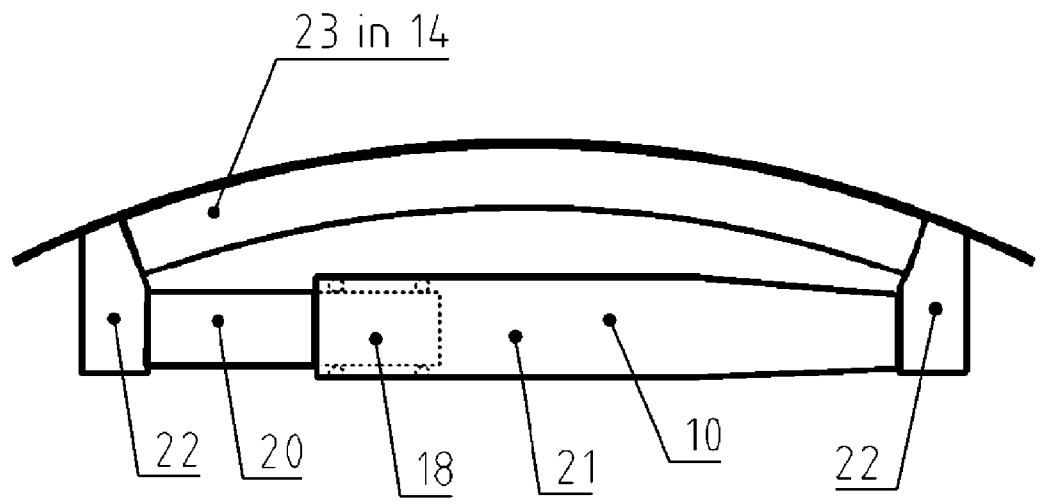
Figure 11:
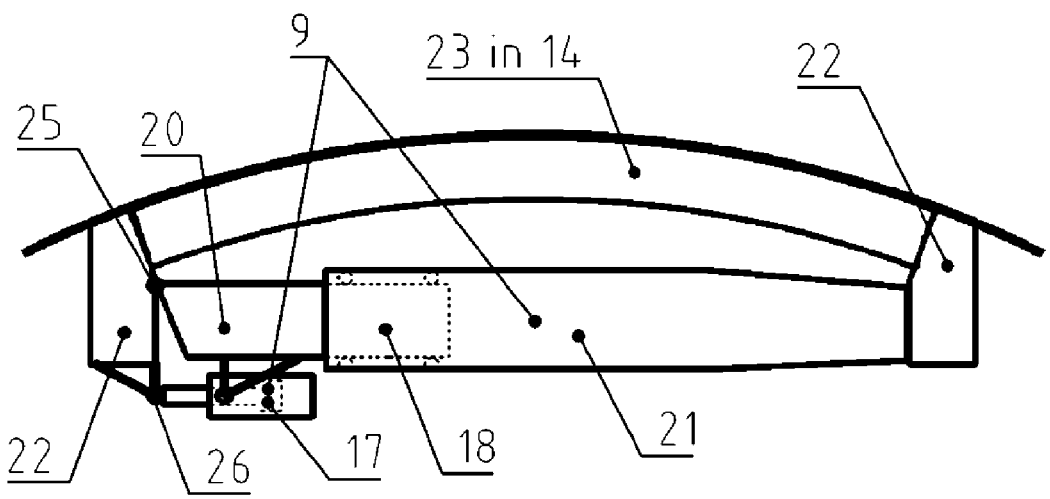

Further details, features and merits of the invention will emerge from the following description of exemplary embodiments, making reference to the corresponding drawings. These show:

FIG. 1: perspective representation of a complementary structure configured as a soft box;

FIG. 2: front view of a complementary structure configured as a soft box;

FIG. 3: schematic cross section of an equivalent cross section configured as a di-box;

FIG. 4: schematic cross section of an equivalent cross section configured as a tri-box;

FIG. 5 configurations of the equivalent cross sections as a) di-, b) tri- and c) tetra-box with correction actuators arranged inside the structure;

FIG. 6a: shell coupler as a tension plate of Y-shape in perspective view;

FIG. 6b: shell coupler as a tension plate of V-shape in perspective view;

FIG. 6c: shell coupler as a tension plate of V-shape in side view;

FIG. 6d: shell coupler as a tension plate of V-shape in top view;

FIG. 7: shell coupler as a membrane with tension rod in perspective view;

FIG. 8a: cross section view of the clamping disk;

FIG. 8b: clamping disk in perspective view;

FIG. 8c: hole pattern of the connection of soft box or shell coupler and the hull shell by means of clamping disk;

FIG. 9: passive frame brace in system of the barrel hull and equivalent cross section;

FIG. 10 schematic of passive frame brace;

FIG. 11 schematic of active frame brace.

FIG. 1 is a perspective view of a complementary structure of the invention in the configuration as a soft box. In the lengthwise direction, this consists of several U-profiles lined up alternatingly next to each other and staggered, the ends of the profile legs 3 being configured with lengthwise flanges 4 to accommodate the hull shell 14 (not shown). The profiles, in concert with the selected hole pattern, have flank intervals between 21 mm and 49 mm. Furthermore, the lengthwise flanges 4 are provided as boundaries of the complementary structure 1 in the transverse direction for applying and absorbing of correction forces. The lengthwise flanges 4 are formed at an angle of $\alpha_{SW}=22°$ to the connection line of the ends of the legs 3—or secant—and hold the test specimen by its brackets. On the lengthwise flanges 4, means are provided for attaching 5 the hull shell 14 to the complementary structure 1.

The boundaries of the box in the lengthwise dimension are formed as transverse flanges 2. The transverse flange 2 is the connection for applying force to the equivalent cross section, i.e., the complementary structure 1 and the hull shell 14 attached to it, hereinafter also termed in general the test specimen. The transverse flange 2 connects the soft box 1 to the testing device in such a way that pressure can be applied to the resulting interior space of the complementary structure joined to the hull shell 14, in order to simulate realistically the pressure gradient for airplanes at high altitudes.

FIG. 2 is a front view of a complementary structure 1 in the configuration of a soft box 1. The cross section shape of the soft box 1 is formed by two quarter ellipses 12, which are joined together by a horizontal segment 11 at their lower major vertex. The transverse flanges 2 are provided at the same time to apply and absorb test forces in six degrees of freedom.

The upper vertex of the ellipsoidal segments 12 is formed by the legs 3, at whose ends are found the lengthwise flanges 4 to hold the hull shells 14. The configuration depicted shows an angle of $\alpha_{SW}=22°$. The angle $\alpha_{SW}=22°$ is related to the contour of the test specimen and stands in a relation $b=R_{ref} \cdot 2 \cdot \sin \alpha_{pü}$ to the spacing of the two legs 3, where $R_{ref}=1978$ and $\alpha_{pü}=22.5°$. The indices "SW", "ref" and "pü" stand for sandwich, reference (e.g., tool radius) and the circular segment exposed to the excess pressure.

Generally, the relation holds $\alpha_{SW}=\alpha_{pü}-0.5°$. It should be mentioned as especially advantageous that thanks to the specific stiffness modeling of the pressure box, the angle $\alpha_{SW}$ changes but little under the loading.

FIG. 3 is a schematic representation of an equivalent cross section in the embodiment of a di-box. By means of two shell couplers 13, corresponding to the complementary structure 1 in the soft box according to FIG. 1 and FIG. 2, two hull shells 14 are joined together into pressure pipes. The angular functions in polygon boxes can generally be written as follows:

$\alpha_{SW}=\alpha_{pü}-0.5°$ level overlapping length $L_{Ü}=f(N_x;N_\psi;N_{x\psi};\mu_0$ clampingdisk)

included angle of the intermediate pieces/complements $\beta=180°-360°/N+2 \cdot \alpha_{SW}$ The minimum distance between two hull shells is chosen at $b_{min}=300$, for convenient access during assembly. A greater width only makes sense if there are assembly difficulties or spatially colliding force application pathways.

FIG. 4 is a schematic cross section with complementary structure in the configuration of a tri-box. Here, three hull shells 14 are joined together by three shell couplers 13 into a pressure pipe. This principle can be expanded in theory to the full cross section. The included angle for the secant in the tri-box is 60°. The angle relations for the tri-box are adequate to the general description as for FIG. 3.

FIG. 5a, FIG. 5b and FIG. 5c present configurations of the equivalent cross sections with complementary structures as di-, tri- and tetra-box with correction actuators 17 arranged inside the structure. The correction actuators 17 apply the correction forces to the hull shells 14 via the shell couplers 13.

For the tetra-box shown in FIG. 5c, the same functions hold as for the tri-box, but the included angle of the secant is increased from 60° to 90°.

FIGS. 6a and 6b show shell couplers 13 as a tension plate in various embodiments. In FIG. 6a, a shell coupler 13 in Y-form is shown. The shell coupler 13 in FIG. 6b is V-shaped in cross section and joined to the hull shell 14 at the free ends of the legs via means for attaching 5, such as a connection via a clamping disk 7. At the acute angle according to FIG. 6a, tension rods 16 engage with the shell coupler 13, by which the correction forces are brought from the outside into the complementary structure 13 and the hull shells 14. When correction force is applied at the inside, the acute angle of FIG. 6b is rounded and provided with discrete thrust-transmitting pieces 19, similar to those in a pressure box of the D-box. FIGS. 6c and 6d show the shell coupler 13 in side view and top view.

FIG. 7 shows a shell coupler 13 as a membrane 15 with tension rod 16. The hull shells 14 are joined both to the membrane 15 and to tension brackets as part of the tension rod via attaching means 5. In this differentiated embodiment of a shell coupler, the test forces are transmitted solely by means of the membrane and the correction forces are applied exclusively by the tension rods 16.

FIG. 8a shows a clamping disk 7 with truncated pyramid elevations 8 in cross section. As an alternative, knurling is possible, but this is not depicted. The clamping disk 7 has a conical form, corresponding to the holes in the lengthwise flanges 4, so that the clamping disk 7 rests in the hole with positive connection. The truncated pyramids 8 are configured so as to substantially increase the coefficient of friction and keep the surface pressure due to installation force reasonably low. Lamination of the funnel shape 6 further lessens or limits the unevenness of the holes. FIG. 8b shows a clamping disk 7 in perspective view.

FIG. 8c shows, as an example, a feature for the preferred embodiment of the means of attachment 5 of the soft box 1 or the shell coupler 13 to the hull shells 14, in cross section. The hull shell 14 lies against the clamping disk 7 around the boreholes for the screw connection, and the disk is arranged with its opposite conical end in the funnel-shaped depression 6 in the lengthwise flange 4 of the soft box 1 or the shell coupler 13.

FIG. 9 shows a passive frame brace 10 in the system of the barrel fuselage and equivalent cross section. The cross section of a barrel fuselage 24 is shown schematically, in order to illustrate the effect from using an equivalent cross section with complementary structure 1. It can be clearly seen that the system of the equivalent cross section with complementary structures leads to a significant reduction in the space requirement for such testing. Hence, material testing for large structures becomes economically efficient. The indicated complementary structure 1 supports the test specimen, the hull shell 14 with the frame 23, and forms with the latter the equivalent cross section. The departure of the equivalent cross section from the barrel fuselage cross section 24 results in unwanted side effects, due to the geometry, which affect the representativeness of the measurements. In order to counteract these effects, a passive frame brace 10 is used, for example.

The passive frame brace 10 is shown in FIG. 10 as an assembly sketch. The frame brace 10 is primarily a means of equalizing the locally eccentric application of tangential forces. Its effect is based on preventing the frame heads from twisting relative to each other. In the passive configuration, therefore, the bending stiffness of the frame brace 10 must be around one order of magnitude higher than that of the skin and frame assembly. At the same time, a smooth, telescopic change in length is made possible by the length adjustment 18 of inner leg 20 and outer leg 21 of the passive frame brace 10. Thus, strain-related changes in the arc dimension of the hull shell 14 in the circumferential direction are passively equalized. The inner leg 20 and the outer leg 21 are each joined by a frame head 22 to the frame 23, which in turn is joined to the hull shell 14.

The principle of the active frame brace 9 is shown in FIG. 11. It corresponds to a widening of the passive frame brace 10. Here, the inner leg 20 is movably connected by a joint 25 to the frame head 22. In addition, a correction actuator 17 is arranged on the inner leg 20, parallel to it, and its piston rod engages with a joint 26, which is also arranged on the frame head 22. Now, if a strain occurs in the circumferential direction of the hull shell due to excess pressure, the inner leg 20 moves out from the length adjustment 18. In order to effectively prevent a twisting of the frame head 22, independently of the bending stiffnesses of the frame braces, the bending moment is now adjusted true to angle or hypercorrected via the joints 25 and 26, by the push/pull of the correction actuator 17.

LIST OF REFERENCE NUMBERS 1 complementary structure "soft pressure box"
2 transverse flange
3 leg
4 lengthwise flange
5 means of attachment
6 funnel-like depression
7 clamping disk
8 truncated pyramids
9 active frame brace
10 passive frame brace
11 horizontal segment
12 ellipsoidal segment, quarter ellipses
13 complementary structure shell coupler
14 hull shell
15 membrane
16 tension rod
17 correction actuator
18 length adjustment
19 thrust-transmitting pieces
20 inner leg
21 outer leg
22 frame head
23 frame
24 cross section of a barrel fuselage
25 joint of inner leg of frame head
26 joint of corrective force actuator of frame head

The invention claimed is:

1. Testing device for hull shells, wherein a test specimen is joined to a complementary structure with legs, having a U-shape in cross section, and at the ends of the legs there are provided lengthwise flanges in the lengthwise direction of the complementary structure with means of attaching the hull shell to the complementary structure and of applying and absorbing of corrective forces, while at the borders of the complementary structure in the lengthwise direction there are provided transverse flanges for applying and absorbing of test forces in six degrees of freedom, characterized in that the complementary structure is formed as a soft box of composite materials and the U-shaped cross section of the complementary structure consists of a horizontal straight segment and two ellipsoidal segments adjoining each side, forming the legs of the U-shaped complementary structure.

2. Testing device according to claim 1, characterized in that the ellipsoidal segments are fashioned as quarter ellipses.

3. Testing device according to claim 1, characterized in that the lengthwise flanges are formed at an angle of $\alpha_{SW} = \alpha_{pü} - 0.5°$ to the horizontal connection line between the legs.

4. Testing device according to claim 1, characterized in that the lengthwise flanges are formed at an angle of $\alpha_{SW} = 22°$ to the horizontal connection line between the legs.

5. Testing device according to claim 1, characterized in that the complementary structure (1)—soft pressure box—is formed from U-profiles alternatingly lined up in the lengthwise direction.

6. Testing device according to claim 1, characterized in that the complementary structure has a material thickness of 13.6 mm.

7. Testing device according to claim 1, characterized in that the complementary structure is constructed from twenty-three individual layers.

8. Testing device according to claim 1, characterized in that the means of attaching the hull shell to the complementary structure consist of a funnel-shaped depression and a correspondingly shaped clamping disk, as well as screws and nuts, there being provided a ribbing of truncated pyramids on the top side of the clamping disk facing the hull shell.

9. Testing device according to claim 1, characterized in that the complementary structure is made from fiberglass-reinforced epoxy resin.

10. Testing device according to claim 1, characterized in that the hull shells are fashioned as frame-reinforced hull shells and a passive frame brace is provided, having an inner and outer leg, connected via a length adjustment, while the passive frame braces are fashioned so as to balance out the locally eccentric application of tangential forces, during which the relative angle between the frame heads remains approximately constant when the hull shell is placed under load.

11. Testing device according to claim 1, characterized in that the hull shells are fashioned as frame-reinforced hull shells and an active frame brace is provided, having an inner and outer leg, connected via a length adjustment, and furthermore the inner leg is connected by a joint to the frame head and a correction actuator is arranged on the inner leg in parallel and connected to the piston rod via a joint with the frame head so that the locally eccentric application of tangential forces can be balanced out and the relative angle between the frame heads remains constant or is hypercorrected under loading of the hull shell, while either the angle or the bending moment is used as the controlled variable and the dependent component is adjusted each time.

12. Testing device for hull shells, wherein a plurality of test specimens comprising hull shells representing only some of a plurality of segments of a hull are joined to a complementary structure comprising a plurality of shell couplers forming together an equivalent cross section less than a cross section of the hull and means are provided for attaching the hull shell to the complementary structure, characterized in that the equivalent cross section is formed from N-hull shells having a total cross section less than the equivalent cross section with N-shell couplers, where N is a whole number larger than 1.

13. Testing device according to claim 12, characterized in that the complementary structure is formed as a shell coupler with a V-shaped cross section, and the V-shaped cross section consists of two straight legs, which are joined together by a rounding, and the rounding contains contact surfaces for applying of correction forces by means of thrust-transmitting pieces.

14. Testing device according to claim 12, characterized in that the complementary structure is formed as a shell coupler with a Y-shaped cross section, and the Y-shaped cross section consists of two straight legs, joined together by a common straight extension, and the extension contains means for applying discrete correcting forces by tension rods.

15. Testing device according to claim 12, characterized in that the equivalent cross section consists of two, three or four hull shells and the corresponding number of shell couplers.

16. Testing device according to claim 12, characterized in that the means of attaching the hull shell to the complementary structure consist of a funnel-shaped depression and a correspondingly shaped clamping disk, as well as screws and nuts, there being provided a ribbing of truncated pyramids on the top side of the clamping disk facing the hull shell.

17. Testing device according to claim 12, characterized in that the complementary structure is made from fiberglass-reinforced epoxy resin.

18. Testing device according to claim 12, characterized in that the hull shells are fashioned as frame-reinforced hull shells and a passive frame brace is provided, having an inner and outer leg, connected via a length adjustment, while the passive frame braces are fashioned so as to balance out the locally eccentric application of tangential forces, during which the relative angle between the frame heads remains approximately constant when the hull shell is placed under load.

19. Testing device according to claim 12, characterized in that the hull shells are fashioned as frame-reinforced hull shells and an active frame brace is provided, having an inner and outer leg, connected via a length adjustment, and furthermore the inner leg is connected by a joint to the frame head and a correction actuator is arranged on the inner leg in parallel and connected to the piston rod via a joint with the frame head so that the locally eccentric application of tangential forces can be balanced out and the relative angle between the frame heads remains constant or is hypercorrected under loading of the hull shell, while either the angle or the bending moment is used as the controlled variable and the dependent component is adjusted each time.

* * * * *

UNITED STATES PATENT AND TRADEMARK OFFICE
CERTIFICATE OF CORRECTION

PATENT NO. : 7,624,695 B2 Page 1 of 1
APPLICATION NO. : 11/693044
DATED : December 1, 2009
INVENTOR(S) : Götze et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this

Twenty-sixth Day of October, 2010

David J. Kappos
*Director of the United States Patent and Trademark Office*